United States Patent [19]
Yoshida

[11] Patent Number: 5,245,424
[45] Date of Patent: Sep. 14, 1993

[54] DEFECT DETECTION METHOD

[75] Inventor: Hajime Yoshida, Tokyo, Japan

[73] Assignee: Hajime Industries Ltd., Tokyo, Japan

[21] Appl. No.: 823,328

[22] Filed: Jan. 21, 1992

[30] Foreign Application Priority Data

Jan. 24, 1991 [JP] Japan ............................... 3-024123

[51] Int. Cl.$^5$ .............................................. H04N 7/18
[52] U.S. Cl. ...................................... 358/106; 358/101
[58] Field of Search ......................... 358/106, 167, 101

[56] References Cited

U.S. PATENT DOCUMENTS 3,775,556 11/1973 Nagamatsu ........................... 358/106
4,486,777 12/1984 Yamamura ........................... 358/106

Primary Examiner—Howard W. Britton
Attorney, Agent, or Firm—Bauer & Schaffer

[57] ABSTRACT

An image of a light irradiated object is picked up by a video camera. Detection of defects on the object is conducted from the image signal from the video camera. Two inspection zones adjacent each other are established on the picture screen, each having a preset size. The brightness of each of the respective two inspection zones is sensed and accumulated as the inspection zones are indexed across the screen. When the difference between the accumulated values of the respective inspection zones exceeds a preset threshold value a defect is defined.

8 Claims, 4 Drawing Sheets

FIG.2A
FIG.2B
FIG.2C
FIG.2D
FIG.3A
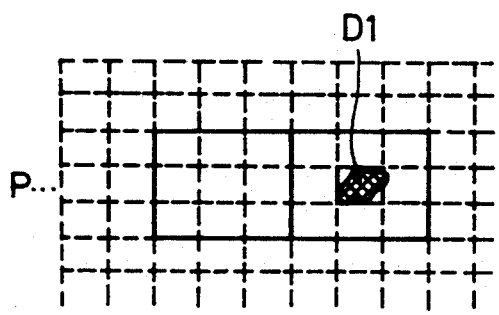
FIG.3B
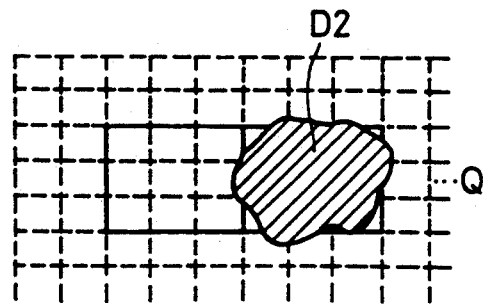

DEFECT DETECTION METHOD

BACKGROUND OF THE INVENTION

1. Field of the Invention

The present invention relates generally to a method and apparatus for the detection of defects on the surface of an object and more particularly, to a method and apparatus suitable for use with a system that employs a video camera, the image signals of which are processed by a computer, to automatically detect defects on inspected objects.

2. Description of the Prior Art

It has become a common practice in recent years, to detect surface defects such as flaws, dirt, or the like, by photosensing the illuminated image of an object undergoing inspection by using a video camera, such as a CCD (charge coupled device) camera, a solid state photosensing element or the like. Generally, the video output signal of the camera is digitized and the photoelectric conversion signals from each of the pixels of the digitized video signal are processed to determine whether a surface defect exists. A comparison of the respective data values obtained to a preset threshold value is the method most generally utilized for determining the existence of a defect.

However, since the brightness contrast of the flaws or dirt varies across the surface of the inspected object, the conventional defect detection methods that operate by digitizing the contrast ratio on the picture screen, make it difficult to detect those defects that exhibit only slight contrast variation from the remaining un-flawed surface. In other words, detection is relatively simple when defects such as black dots, having great contrast variation from the background are sensed on the picture screen so that the difference in contrast data as compared to the background is large, but detection is difficult when surface flaws, or the like, exhibit only subtle contrast variation from the background. This problem is exacerbated when the flawed area is large, due to the subtle difference of its data value to the background.

Previous attempts to detect defects exhibiting only minor contrast variation from the background involve acknowledging the subtle difference in data value as a defect. However, such systems will also cause the sensing of slight indentations or lumps that produce slight intensity changes against the background to be determined as defects, though they may be representative of good product. Thus, it has proven difficult to accurately detect low contrast defects as representative of bad product. Consequently, the problem of a high good product rejection rate has not been solved.

OBJECTS AND SUMMARY OF THE INVENTION

Accordingly, it is an object of the present invention to provide a defect detection method and an apparatus thereof that will enable positive and stable detection of defects exhibiting low brightness contrast in comparison to the background.

According to one aspect of the present invention, there is provided a defect detection method in which an image of a light irradiated object is picked up by a video camera and defect detection is conducted on the basis of an image signal from the video camera, which comprises the steps of:

setting up two inspection zones which are adjacent each other and have a preset size on the picture screen formed by the image signal;

accumulating the brightness of each of said respective two inspection zones over the entire picture screen; and determining the presence of a defect when the difference between the accumulated values exceeds a preset threshold value.

According to another aspect of the present invention, there is provided a defect detection apparatus in which an image of a light irradiated object is picked up by a video camera and defect detection of the inspected object is conducted on the basis of an image signal from the video camera, which apparatus comprises:

means for setting up two inspection zones adjacent each other and having a preset size on a picture screen formed by the image signal;

means for accumulating brightness of each of said respective two inspection zones over the entire picture screen; and means for determining the presence of a defect when the difference between the accumulated values exceeds a preset threshold value.

BRIEF DESCRIPTION OF THE DRAWINGS

A better understanding of the objects, features and advantages of the present invention can be gained from a consideration of the following detailed description of the preferred embodiments thereof, in conjunction with the FIGURES of the accompanying drawings, wherein:

FIGS. 2A through 2D are explanatory diagrams showing the data signal functions of the embodiment of FIG. 1;

FIGS. 3A and 3B are explanatory diagrams showing defects overlapped on pixels;

DESCRIPTION OF THE PREFERRED EMBODIMENTS

Figure 1:
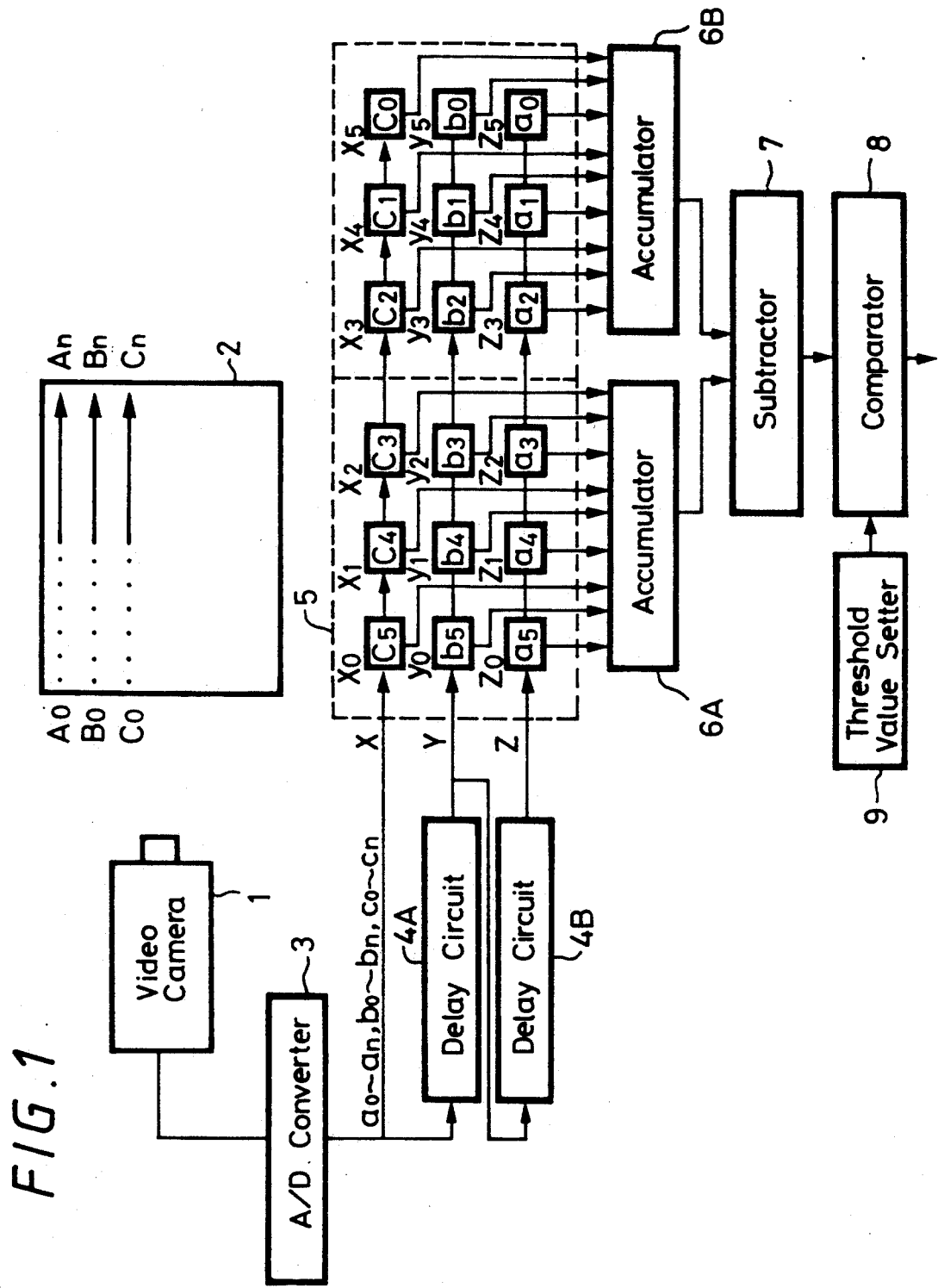
FIG. 1 is a block diagram showing an embodiment of a defect detection apparatus employing the method of the present invention.

An embodiment of the defect detection method and apparatus in accordance with the present invention shall be explained with reference to the attached drawings where like elements are identified with the identical reference numerals throughout.

In FIG. 1, reference numeral 1 designates a known video camera that is used to view the surface of an inspected object (now shown), and reference numeral 2 designates a target or picture screen associated with the video camera 1 which is used to illustrate the scanning operation of the video camera 1. As illustrated, pixels A0 to An of a first row are horizontally scanned, followed sequentially by the horizontal scanning of pixels B0 to Bn of the second row, pixels C0 to Cn of the third row, and so on. Reference numeral 3 designates an Analog-to-Digital (A/D) converter which is connected to the output terminal of the video camera 1, and which converts the respective pixel voltages thereof to data signals that are expressed with digital values such as a0–an, b0–bn, co–cn . . . . The output terminal of A/D converter 3 is connected to the input terminal X of a data shift register 5 and to the input terminal of a delay circuit 4A, where the output terminal of delay circuit 4A is connected to the input terminal Y of a data shift register 5. As the delay circuit 4, a commercial product such as an LSI line filter, or digital filter processor, or the like, may be used and for the data shift register 5, a commercial LSI digital filter, digital signal processor, or the like, may be used The delay circuit 4A delays the data signal for a period equal to one horizontal scanning period and outputs the same, whereas data shift register 5 shifts and sends the digital data signal sequentially through the individual register cells in synchronism with the scanning of the video camera 1. The structure of the data shift register 5 comprises 3 rows of individual cells, for a total of 18 individual cells, i.e., x0–x5, y0–y5, and z0–z5, as shown in FIG. 1. All of the data signals held in the respective register units can be extracted through the respective taps, or pins of the shift register (not shown).

The operation of the defect detection system of FIG. 1 will now be explained. As shown in FIG. I, the inspection zones comprise adjacent lattice like zones, each of which includes 3 pixels in the horizontal direction and 3 pixels in the vertical direction, or 3×3 (9 pixels) each, for a total of 9 pixels ×2. It should be obvious to those skilled in the art, however, that only slight variation in circuit structure is necessary in order to accomodate any of a variety of inspection zones. For example, inspection zones having 2×2 (4 pixels), or 4×4 (16 pixels), etc., may be more desirable, depending upon the inspection purposes.

The output terminal of delay circuit 4A is connected to the input terminal of delay circuit 4B which is of the same structure as delay circuit 4A and is also connected to the input terminal Y of the data shift register 5. Further, the output terminal of delay circuit 4B is connected to an input terminal Z of data shift register 5. The taps of register units X0–X2, Y0–Y2 and Z0–Z2 that are located at the left side of data shift register 5 are connected to the input terminals of accumulator 6A, whereas the taps of register unit X3–X5, Y3–Y5 and Z3–Z5 that are located at the right side of the data shift register 5 are connected to the input terminals of accumulator 6B. The output terminals of a subtractor 7 and the output terminal of subtractor 7 is connected to a comparator 8 to which is connected a threshold value setter 9.

The operation of the circuit of FIG. 1 will now be described in the case of a data signal (a0,-an, . . .) with reference to FIG. 2.

In FIG. 2, the horizontal direction lineup of pixels A0–An, B0–Bn, C0–Cn, ..., of the photosensing area or target screen 2 of the video camera 1 are shown. The data signal is converted to a digital signal via A/D converter 3. The digitized signal, representative of the generated voltages at respective pixels, shall be a0–an, b0–bn, . . . . Accordingly, while the pixels A0–An, B0–n, C0–Cn, . . . of the target, or screen 2 of the video camera 1 are scanned, the corresponding digital data signals a0–an, b0–bn, . . . are output from the A/D converter 3.

The data signals a0–an, . . . , as output from the A/D converter 3 are applied to the input terminal X of data shift register 5 and to the input terminal of delay circuit 4A in the sequence of a0–an, b0–bn, . . . . Therefore, when the data signals pass the delay circuits 4A, 4B and the data shift register 5, and when the data signal a0 arrives at the final register unit z5 of the data shift register 5, as illustrated in FIG. 1, the lineup of the data signals at the respective register units become as shown in FIG. 2A.

In other words, the data signals corresponding to the pixels A0–A2, B0–B2, C0–C2, and A3–A5, B3–B5, C3–C5 within the two inspection zones L and R, as encircled by solid lines in FIG. 2A, are lined up horizontally in sequence. Next, when data signal a1 is sent to register unit z5, it appears as shown in FIG. 2B so that the data signals corresponding to pixels A1–A3, B1–B3, C1–C3, and A4–A6, B4–B6, C4–C6 shall be horizontally lined up in sequence. In a similar manner, when data signal a2 is transferred to register unit z5, the status will be as shown in FIG. 2C. This process is carried out in an iterative fashion until the inspection zones L, R have sequenced horizontally across the screen. When one horizontal scan is completed, the next horizontal scans runs as in FIG. 2D, in which a similar function is repeated, starting now at the second row of pixels, i.e., pixel B0. In this manner, the entire picture screen 2 is scanned by the two inspection zones L, R.

By scanning in this manner, the respective register unit data can be extracted from the respective taps thereof so that the data from the two inspection zones L, R are respectively fed to the accumulators 6A and 6B at each position of the inspection zones, where the data gross accumulation values are respectively accumulated.

As the next step, the two sets of data gross accumulation values are sent from the accumulators 6A and 6B to the subtractor 7 to determine the difference between the two data gross accumulation values which is then sent to the comparator 8. At this comparator 8, comparison between the preset threshold value as set by the threshold value setter 9 and the difference between the two data gross accumulation values as derived from subtractor 7 is made. When the difference between the two data gross accumulation values exceeds the preset threshold value, a judgement signal is output to indicate the existence of a defect. The difference in gross accumulation values for the two data sets is compared with the threshold value as an absolute value.

Figure 4A:
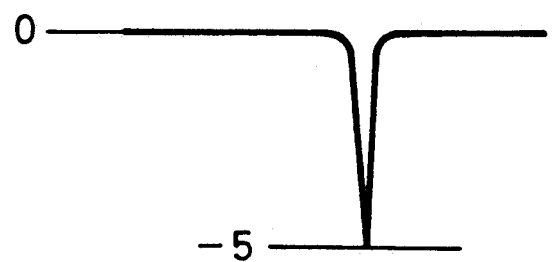
FIGS. 4A and 4B are graphic diagrams showing the voltage level of the pixels related to the defects of FIGS. 3A and 3B.
Figure 4B:
Figure 5A:
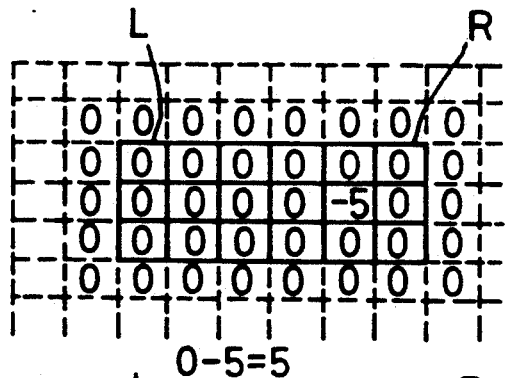
FIGS. 5A through 5D are explanatory diagrams showing the defect detection method of the preferred embodiment shown in FIG. 1.
Figure 5B:
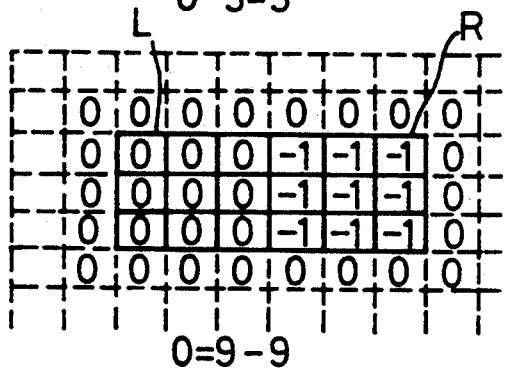

FIG. 3A illustrates a small black dot D1 on the surface of an inspected object and FIG. 3B shows a faint dirty spot D2 on the surface of the inspected object that should be judged as a defect due to the large area thereof, both of which defects are respectively placed so as to overlap pixels. FIGS. 4A and 4B show the voltage levels of pixel lines P . . . Q in FIGS. 3A and 3B. Generally, the background surface level is bright and the black dot D1 and faint dirty spot D2 are darker than the background. The background level may be normalized to zero, and the defects having negative values. Now, taking the black dot D1 level as −5 and the faint dirty spot D2 level as −1 as shown in FIGS. 4A and 4B, they will be represented within the two inspection zones L, R as shown in FIGS. 5A and 5B, respectively. FIG. 5A indicates the black dot portion D1 and FIG. 5B indicates the faint dirty portion D2, respectively. Therefore, the difference of the gross accumulated values within the two inspection zones L, R at FIG. 5A aggregates to 5, while the same difference is 9 in the case of FIG. 5B. In such case, if the threshold value at the threshold value setter 9 is, for example, setup within the range of 6–8, it will be possible to neglect the black dot D1 and only detect the faint dirty portion D2.

Figure 5C:
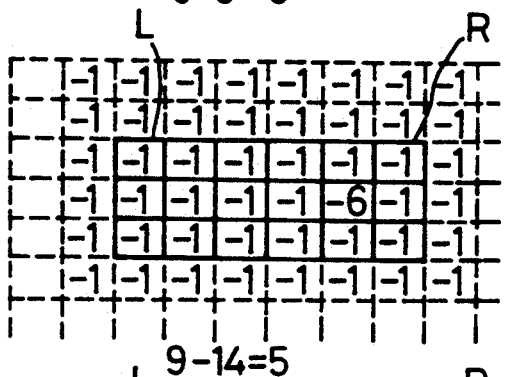
Figure 5D:
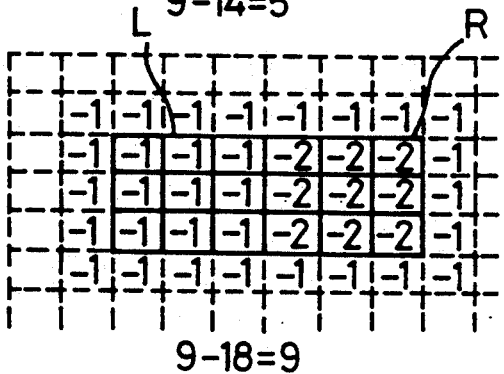

In the case of FIGS. 5A and 5B, the background level was setup assuming it to be 0, but when the background level slightly varies to the dark side such as −1, and if the black dot D1 and faint dirty spot D2 levels against the background level are the same −5 and −1, the actual values thereof becomes −6 and −2. Therefore, as shown in FIGS. 5C and 5D, the differences of the gross accumulated values within the two inspection zones L, R becomes 5 and 9 which will be the same case as in FIGS. 5A and 5B, which shows that stable judgement processing of the faint dirty spot D2 detection is maintained even though the background level varies.

According to the embodiment of the present invention as above described, such faint dirty areas that were extremely difficult to detect by conventional methods, or defects that show only slight brightness contrast against the background can be positively detected with stability, which, as a result, will prevent the good product yield deterioration after inspection is conducted.

Further, since the inspection zone size may be optionally set up in accordance with the inspection purposes as previously mentioned, a plurality of processing circuits that have different inspection zones may be provided as an example, so that a consolidated defect judgement based on the respective detection results can be made.

Further, in accordance with the embodiment of the present invention, by utilizing the various LSI exclusive processors on the market as image processors, it will be easy and simple to construct the inventive system with commercially available components at a relatively low cost.

Also, with the method and apparatus of the present invention, since high speed defect detection processing may be performed, high volume, real-time inspection of objects that are moving on a conveyor belt at high speeds can be made possible using the present invention, resulting in its practical merit in real line use.

The present invention may be placed into practical use, since the aforementioned various LSI processors for exclusive image processing can be utilized, by appropriately programming the computer software and, it is therefore apparent that a system may be easily constructed.

It should be understood that the above description is presented by way of example of the preferred embodiments of the invention and it will be apparent that many modifications and variations thereof could be effected by one with ordinary skill in the art without departing from the spirit and scope of the novel concepts of the invention so that the scope of the invention should be determined only by the appended claims.

I claim as my invention:

1. A method for the detection of defects in the surface of an object in which an image of the object is picked up by a video camera having output image signal adapted to define an image on a screen having an array of pixels, said method comprising the steps of;
    setting up two adjacent inspection zones each comprising a plurality of pixels and simultaneously indexing said zones across the pixel array;
    accumulating within each zone the brightness of all of the pixels within the zone; and
    judging the accumulated brightness in each position into which said adjacent inspection zones are indexed and detecting when the difference between the accumulated values exceeds a preset threshold value.

2. A defect detection method as claimed in claim 1, wherein the size of said two inspection zones is variable.

3. A defect detection method as claimed in claim 1, wherein said preset threshold value is variable.

4. A defect detection method as claimed in claim 1, wherein said two inspection zones are equal in size.

5. A defect detection apparatus in which an image of a light irradiated object is picked up by a video camera having an output image signal adapted to define an image on a screen having an array of pixels, said apparatus comprising;
    means for establishing two adjacent inspection zones each comprising a plurality of pixels;
    means for simultaneously indexing said inspection zones across the pixel array;
    means for accumulating within each zone the brightness of all of the pixels within the zone; and
    means for judging the accumulated brightness in each position into which said adjacent inspection zones are indexed and for determining when the difference between the accumulated values exceeds a preset threshold value.

6. A defect detection apparatus as claimed in claim 5, wherein the size of said two inspection zones is variable.

7. A defect detection apparatus as claimed in claim 5, wherein said two inspection zones are equal in size.

8. A defect detection apparatus as claimed in claim 5, wherein two inspection zones are equal in size.

* * * * *